United States Patent
Mori (10) Patent No.: US 9,633,913 B2
(45) Date of Patent: Apr. 25, 2017

(54) METHOD OF EVALUATING EPITAXIAL WAFER

(71) Applicant: SUMCO CORPORATION, Tokyo (JP)

(72) Inventor: Keiichiro Mori, Saga (JP)

(73) Assignee: SUMCO CORPORATION, Tokyo (JP)

( * ) Notice: Subject to any disclaimer, the term of this patent is extended or adjusted under 35 U.S.C. 154(b) by 0 days.

(21) Appl. No.: 15/093,079

(22) Filed: Apr. 7, 2016

(65) Prior Publication Data
US 2016/0307810 A1   Oct. 20, 2016

(30) Foreign Application Priority Data

Apr. 14, 2015 (JP) .................. 2015-082255

(51) Int. Cl.
| | |
|---|---|
| *G01N 21/00* | (2006.01) |
| *H01L 21/66* | (2006.01) |
| *G01N 21/88* | (2006.01) |
| *G01N 21/94* | (2006.01) |
| *G01N 21/95* | (2006.01) |

(52) U.S. Cl.
CPC ......... *H01L 22/12* (2013.01); *G01N 21/8806* (2013.01); *G01N 21/94* (2013.01); *G01N 21/9501* (2013.01); *G01N 2021/8825* (2013.01); *G01N 2021/8845* (2013.01); *G01N 2201/06113* (2013.01)

(58) Field of Classification Search
CPC .... G01J 3/02; G01J 3/513; G01J 3/51; G01N 15/1459; G01N 21/65
USPC .......................................... 356/73
See application file for complete search history.

(56) References Cited

U.S. PATENT DOCUMENTS

| | | | | |
|---|---|---|---|---|
| 5,995,218 A | * | 11/1999 | Ide ...................... | G01N 21/9501 356/237.1 |
| 6,153,444 A | * | 11/2000 | Nakano .............. | G01R 31/2656 257/E21.53 |

(Continued)

FOREIGN PATENT DOCUMENTS

| | | |
|---|---|---|
| JP | 2001-153635 A | 6/2001 |
| JP | 2004-531735 A | 10/2004 |
| JP | 3664134 B2 | 4/2005 |

(Continued)

OTHER PUBLICATIONS

Office Action issued in Japan Patent Appl. No. 2015-082255, dated Mar. 15, 2016, together with an English language translation.

(Continued)

*Primary Examiner* — Tarifur Chowdhury
*Assistant Examiner* — Md M Rahman
(74) *Attorney, Agent, or Firm* — Greenblum & Bernstein, P.L.C.

(57) ABSTRACT

The method of evaluating an epitaxial wafer includes performing evaluation of an epitaxial wafer by detecting, as a light point defect, an abnormal substance selected from the group consisting of a defect and a surface deposit of an epitaxial wafer to be evaluated with a surface inspection apparatus including two types of incidence systems with different incidence angles and two types of light receiving systems with different light receiving angles, based on two types of measurement results.

16 Claims, 2 Drawing Sheets

(56) References Cited

U.S. PATENT DOCUMENTS

| | | | | |
|---|---|---|---|---|
| 6,726,319 B1 * | 4/2004 | Yanase | ................... | G01N 21/47 |
| | | | | 250/559.27 |
| 2012/0194807 A1 * | 8/2012 | Maruyama | ......... | G01N 21/9501 |
| | | | | 356/237.2 |

FOREIGN PATENT DOCUMENTS

| | | |
|---|---|---|
| JP | 2009-236791 | 10/2009 |
| JP | 2010-129748 A | 6/2010 |
| JP | 2012-068103 A | 4/2012 |
| WO | 03/001186 A1 | 1/2003 |

OTHER PUBLICATIONS

Office Action issued in Japan Patent Appl. No. 2015-082255, dated Aug. 9, 2016.

* cited by examiner

METHOD OF EVALUATING EPITAXIAL WAFER

CROSS-REFERENCE TO RELATED APPLICATIONS

This application claims the benefit of priority under 35 USC 119 to Japanese Patent Application No. 2015-082255 filed on Apr. 14, 2015, which is expressly incorporated herein by reference in its entirety.

BACKGROUND OF THE INVENTION

Field of the Invention

The present invention relates to an evaluation method and evaluation apparatus of an epitaxial wafer, and, in an aspect, relates to an evaluation method and evaluation apparatus of an epitaxial wafer that are capable of detecting, with a high sensitivity, defects and/or foreign substances of various shapes and sizes.

Furthermore, the present invention relates to epitaxial wafer which the evaluation according to the evaluation method has been performed.

Discussion of the Background

Methods based on a light point defect (LPD) that is detected with a laser surface inspection apparatus are widely used as an evaluation method of defects and/or foreign substances of a semiconductor wafer (for example, see Japanese Patent No. 3664134 or English language family member U.S. Pat. No. 6,726,319, Published Japanese translation of PCT patent application No. 2004-531735 or English language family member WO2003/001.186, Japanese Unexamined Patent Publication (KOKAI) No. 2010-129748, and Japanese Unexamined Patent Publication (KOKAI) No. 2001-153635, which are expressly incorporated herein by reference in their entirety). In the above methods, by causing light to enter a surface of a wafer to be evaluated and by detecting radiation light (scattered light and reflected light) from the surface, the presence or absence of defects of the wafer and/or foreign substances adhering to the surface, that is, surface deposits, of the wafer as well as the size thereof can be evaluated.

SUMMARY OF THE INVENTION

In the above publications, there is proposed detection of different types of defects and/or foreign substances by combining a plurality of incidence systems and/or a plurality of light receiving systems.

On the other hand, in an epitaxial wafer, defects and/or foreign substances of various shapes and sizes may exist. If these defects and/or foreign substances can be detected with higher sensitivity, an epitaxial wafer with a fewer defects and/or foreign substances can be provided by managing a manufacturing process such as eliminating causes of generation of defects and/or foreign substances on the basis of the detection result.

An aspect of the present invention provides for an evaluation method that can detect, with a high sensitivity, defects and/or foreign substances of an epitaxial wafer.

A laser surface inspection apparatus includes at least one incidence system and at least one light receiving system. As to the incidence system, there are an incidence system that makes light incident onto a wafer surface from a high angle side (for example, from the vertical direction) and an incidence system that makes light incident onto a wafer surface from a low angle side (oblique direction). In the same way as for the light receiving system that receives radiation light, there are a light receiving system that receives light from a high angle side and a light receiving system that receives light from a low angle side.

When summing up the above points, the following four combinations can be adopted as to combinations of the incidence system and the light receiving system:
high angle incidence and high angle light reception
high angle incidence and low angle light reception
low angle incidence and low angle light reception
low angle incidence and high angle light reception On the other hand, in recent years, as to laser surface inspection apparatuses, those that use visible light, ultraviolet light, or light in the intermediate wavelength region thereof, as incident light, have been proposed. Examples of these include Surfscan Series SP1 as an apparatus that uses visible light as incident light, Surfscan Series SP3 as an apparatus that uses ultraviolet light, and Surfscan Series SP2 as an apparatus that uses light in the intermediate wavelength region thereof, all of which are manufactured by KLA TENCOR.

The present inventor conducted extensive research in order to achieve the above-described evaluation method on the basis of above points and obtained the following new findings.

(1) Defects and/or foreign substances having a relatively small size can be detected with high sensitivity by using ultraviolet light as incident light and by a combination of low angle incidence and low angle light reception.

(2) In contrast, defects and/or foreign substances having a relatively smooth convex or concave shape and a large size cannot be sufficiently detected by the evaluation using ultraviolet light as incident light, but can be detected with high sensitivity by using visible light as incident light and by a combination of high angle incidence and high angle light reception.

This can be considered to be caused by the fact that minuter defects and/or foreign substances can be detected with high sensitivity by using ultraviolet light having a short wavelength, but that, since linearity of light becomes intensive when wavelengths become short, most of light with which smooth defects and/or foreign substances are irradiated is specularly reflected and such defects and/or foreign substances become hardly detectable by radiation light (among others, light scattering).

An aspect of the present invention was devised on the basis of the above findings.

An aspect of the present mention relates to a method of evaluating an epitaxial wafer below:

A method of evaluating an epitaxial wafer, which includes performing evaluation of an epitaxial wafer by detecting, as a light point defect, an abnormal substance selected from the group consisting of a defect and a surface deposit of an epitaxial wafer to be evaluated with a surface inspection apparatus including two types of incidence systems with different incidence angles and two types of light receiving systems with different light receiving angles, based on a measurement result 1 and a measurement result 2 below, wherein, among the two types of incidence systems, the incidence system with an incident angle smaller than the incident angle of the other incidence system is referred to as a low angle side incidence system and the other incidence system is referred to as a high angle side incidence system, and among the two types of light receiving systems, the light receiving system with a light receiving angle smaller than the light receiving angle of the other light receiving system is referred to as a low angle side light receiving system and the other light receiving system is referred to as a high angle side light receiving system, measurement result 1: a measurement result based on low angle incidence and low angle light reception, obtained by causing ultraviolet light to enter a surface of an epitaxial wafer to be evaluated from the low angle side incidence system and by receiving radiation light from the surface on the low angle side light receiving system;

measurement result 2: a measurement result based on high angle incidence and high angle light reception, obtained by causing visible light to enter a surface of an epitaxial wafer to be evaluated from the high angle side incidence system and by receiving radiation light from the surface on the high angle side light receiving system.

In an embodiment, the high angle incidence and high angle light reception is performed in a direction vertical to the surface of an epitaxial wafer to be evaluated.

In an embodiment, the abnormal substance is selected from the group consisting of an epitaxial layer-derived defect and a non-epitaxial layer-derived foreign substance.

In an embodiment, the above method further includes distinguishing a non-epitaxial layer-derived foreign substance, Hillock, Stacking Fault, and Dislocation by:

presence or absence detection and a detection size in the measurement result 1; and presence or absence of detection and a detection size in the measurement result 2.

In an embodiment, the distinguishing includes determining an abnormal substance detected only in the measurement result 1 as a non-epitaxial layer-derived foreign substance and/or determining an abnormal substance detected only in the measurement result 2 as Hillock.

In an embodiment, the distinguishing is performed, based on a correlation equation 1: $y_1 = ax_1$ b obtained by fitting plots, the detection size of which in the measurement result 1 is within a first range, and a correlation equation 2: $y_2 = cx_2 + d$ obtained by fitting plots, the detection size of which in the measurement result 1 is within a second range that is a range larger than the first range among plots, the plots being obtained by taking detection size in the measurement result 1 on an X-axis and taking the detection size in the measurement result 2 on a Y-axis, according to the standard shown in Table 1 described further below.

In an embodiment, the first range is a range of more than 0 μm and less than 0.1 μm, and the second range is a range of equal to or more than 0.1 μm and equal to or less than 0.2 μm.

A further aspect of the present invention relates to an apparatus of evaluating an epitaxial wafer, which includes two types of incidence systems with different incidence angles and two types of light receiving systems with different light receiving angles, and which is used in the above evaluation method.

A further aspect of the present invention relates to an epitaxial wafer having been subjected to evaluation by the above evaluation method.

According to an aspect of the present invention, highly sensitive detection of various abnormal substances of an epitaxial wafer becomes possible.

Furthermore, according to an aspect of the present invention, highly sensitive detection and distinction of an epitaxial layer-derived defect and a non-epitaxial layer-derived foreign substance of an epitaxial wafer become possible.

Other exemplary embodiments and advantages of the present invention may be ascertained by reviewing the present disclosure and the accompanying drawing.

BRIEF DESCRIPTION OF THE DRAWINGS

The present invention will be described in the following text by the exemplary, non-limiting embodiments shown in the figure, wherein.

DETAILED DESCRIPTION OF THE EMBODIMENTS

Unless otherwise stated, a reference to a compound or component includes the compound or component by itself, as well as in combination with other compounds or components, such as mixtures of compounds.

As used herein, the singular forms "a," "an," and "the" include the plural reference unless the context clearly dictates otherwise.

Except where otherwise indicated, all numbers expressing quantities of ingredients, reaction conditions, and so forth used in the specification and claims are to be understood as being modified in all instances by the term "about" Accordingly, unless indicated to the contrary, the numerical parameters set forth in the following specification and attached claims are approximations that may vary depending upon the desired properties sought to be obtained by the present invention. At the very least, and not to be considered as an attempt to limit the application of the doctrine of equivalents to the scope of the claims, each numerical parameter should be construed in light of the number of significant digits and ordinary rounding conventions.

Additionally, the recitation of numerical ranges within this specification is considered to be a disclosure of all numerical values and ranges within that range. For example, if a range is from about 1 to about 50, it is deemed to include, for example, 1, 7, 34, 46.1, 23.7, or any other value or range within the range.

The following preferred specific embodiments are, therefore, to be construed as merely illustrative, and non-limiting to the remainder of the disclosure in any way whatsoever. In this regard, no attempt is made to show structural details of the present invention in more detail than is necessary for fundamental understanding of the present invention; the description taken with the drawings making apparent to those skilled in the art how several forms of the present invention may be embodied in practice.

Method Of Evaluating Epitaxial Wafer

An aspect of the present invention relates to a method of evaluating an epitaxial wafer (hereinafter, also referred to as "evaluation method"), which includes performing evaluation of an epitaxial wafer by detecting, as a light point defect, an abnormal substance selected from the group consisting of a defect and a surface deposit of an epitaxial wafer to be evaluated with a surface inspection apparatus including two types of incidence systems with different incidence angles and two types of light receiving systems with different light receiving angles, based on a measurement result 1 and a measurement result 2 below, wherein, among the two types of incidence systems, the incidence system with an incident angle smaller than the incident angle of the other incidence system is referred to as a low angle side incidence system and the other incidence system is referred to as a high angle side incidence system, and among the two types of light receiving systems, the light receiving system with a light receiving angle smaller than the light receiving angle of the other light receiving system is referred to as a low angle side light receiving system and the other light receiving system is referred to as a high angle side light receiving system.

<Measurement result 1> A measurement based on low angle incidence and low angle light reception, obtained by causing ultraviolet light to enter a surface of an epitaxial wafer to be evaluated from the low angle side incidence system and by receiving radiation light from the surface on the low angle side light receiving system.

<Measurement result 2> A measurement result based on high angle incidence and high angle light reception, obtained by causing visible light to enter a surface of an epitaxial wafer to be evaluated from the high angle side incidence system and by receiving radiation light from the surface on the high angle side light receiving system.

The above evaluation method will be described in more detail below.

<Wafer to be Evaluated>

A wafer to be evaluated in the above evaluation method is a wafer having an epitaxial layer on a semiconductor wafer, that is, an epitaxial wafer. Preferably, the wafer to be evaluated is a silicon epitaxial wafer having an epitaxial layer on a silicon wafer. In an epitaxial wafer, various types of abnormal substances, which are selected from the group consisting of defects and surface deposits, may exist. In such abnormal substances, those having various shapes and/or sizes may be included resulting from causes of generation thereof and the like. According to the above evaluation method, detection and distinction of various types of abnormal substances can be performed on the basis of the measurement result 1 and the measurement result 2. Details will be described later.

<Surface Inspection Apparatus>

A surface inspection apparatus used in the above evaluation method includes:

two types of incidence systems with different incidence angles; and two types of light receiving systems with different light receiving angles.

Figure 1:
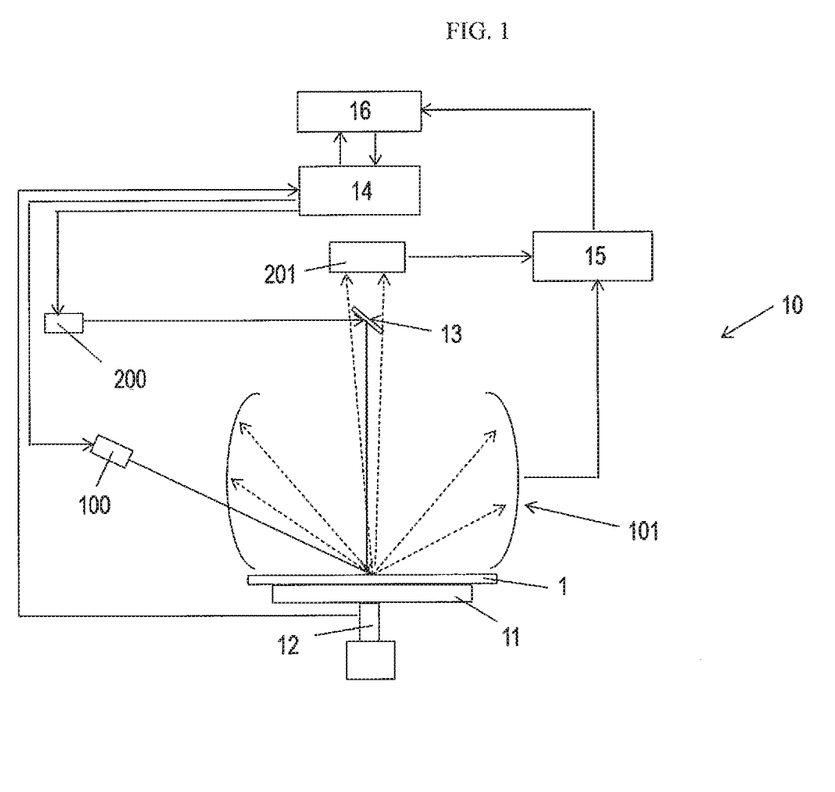
FIG. 1 shows an example (schematic configuration view) of a surface inspection apparatus.

An example (schematic configuration view) of a surface inspection apparatus provided with such incidence systems and light receiving systems is shown in FIG. 1. In FIG. 1, incident light is schematically shown by a solid line arrow and radiation light is schematically shown by a dotted line arrow, but the incidence direction and radiation direction shown in the drawing are exemplifications and do not limit the present invention in any way.

As the incidence systems and the light receiving systems, a surface inspection apparatus 10 shown in FIG. 1 is provided with:

a laser light source (ultraviolet light source) 100 for obtaining the measurement result 1;

a low angle side light receiving part 101 that receives radiation light radiated by scattering or reflection of incident light from the laser light source 100, on a surface of the epitaxial wafer 1;

a laser light source (visible light source) 200 for obtaining the measurement result 2; and a high angle side light receiving part 201 that receives radiation light radiated by scattering or reflection of incident light from the laser light source 200, on a surface of the epitaxial wafer 1.

In the surface inspection apparatus 10 shown in FIG. 1, the low angle side light receiving part 101 has a configuration of receiving radiation light over the entire circumference above a stage 11. However, it suffices for the low angle side light receiving part 101 to have a configuration of being able to receive radiation light and it is not limited to the embodiment shown in FIG. 1.

Furthermore, the surface inspection apparatus 10 is provided with a rotation motor 12 that makes the stage 11 for placing the epitaxial wafer 1 rotatable and with a unit configured to make the stage movable in horizontal directions (not shown), and thus an irradiation position with light incident from each of the laser light sources can be varied. Thereby, it becomes possible to sequentially irradiate (scan), with light, regions to be evaluated of the surface of the epitaxial wafer 1 or the entire region, and to perform the detection of abnormal substances in regions to be evaluated or the entire region of the surface.

The surface inspection apparatus 10 is provided with a mirror 13 for adjusting an incidence angle of light emitted from the laser light source 200 to the epitaxial wafer surface. In the embodiment shown in FIG. 1, a mirror for light emitted from the laser light source 200 is provided, but the mirror 13 may be unnecessary depending on the arrangement position of the laser light source 200. Furthermore, the surface inspection apparatus 10 may be provided with a mirror for adjusting the incidence angle of light emitted from the laser light source 100 to the epitaxial wafer surface, depending on the arrangement position of the laser light source 100.

The surface inspection apparatus 10 is further provided with a control part 14 that controls the rotation and horizontal movement of the stage 11, and a calculation part 15 that calculates the detection size of a detected abnormal substance on the basis of the information of radiation light received by each of the light receiving parts. In addition, a PC (Personal Computer) 16 receives positional information of a position that is irradiated with light from the control part 14, and transmits signal for moving the stage 11 in order to irradiate positions not having been irradiated, with light. Furthermore, the PC 16 can receive information on the detection size of a detected abnormal substance from the calculation part 15, and can generate the measurement result 1 and the measurement result 2.

The surface inspection apparatus 10 can be configured, in an embodiment, by combining commercially available surface inspection apparatuses. For example, the Surfscan Series SP3 manufactured by KLA TENCOR can be used as a commercially available surface inspection apparatus provided with a an incidence system and/or light receiving system for obtaining the measurement result 1, and the Surfscan Series SP1 manufactured by KLA TENCOR can be used as a commercially available surface inspection apparatus provided with an incidence system and/or light receiving system for Obtaining the measurement result 2.

In another embodiment, the surface inspection apparatus may be one provided with a white light source as a single light source. Light (white light) emitted from the white light source is emission light including light of various wavelengths in ultraviolet light and visible light regions. A surface inspection apparatus provided with a white light source that emits white light as a single light source can give ultraviolet light for obtaining the measurement result 1 and visible light for obtaining the measurement result 2 by being further provided with a spectroscope that splits ultraviolet light and visible light from white light. Each of incidence angles of ultraviolet light and visible light to an epitaxial wafer surface can be adjusted by arranging a mirror in the surface inspection apparatus.

<Specific Embodiment of Evaluation Method>

Next, an specific embodiment of the above evaluation method that uses the evaluation result 1 and the evaluation result 2 will be described.

(Wavelength of Incident Light)

The measurement result 1 is a measurement result obtained by using ultraviolet light as incident light, and the evaluation result 2 is a measurement result obtained by using visible light as incident light. Ultraviolet light in the present invention means light within the wavelength region of less than 400 nm, and visible light means light in the wavelength region of 400 nm to 600 nm. As examples, light having a wavelength of 266 nm can be used as ultraviolet light, and light having a wavelength of 488 nm can be used as visible light, but is not limited thereto.

(Incidence Direction and Light receiving Direction)

The measurement result 1 is a measurement result according to low angle incidence and low angle light reception, which is obtained by causing ultraviolet light to enter a surface of an epitaxial wafer to be evaluated from a low angle side and by receiving radiation light from the surface on a low angle side. In contrast, the measurement result 2 is a measurement result according to high angle incidence and high angle light reception, which is obtained by causing visible light to enter a surface of an epitaxial wafer to be evaluated from a high angle side and by receiving radiation light from the surface on a high angle side. The incidence from a low angle side in the present invention means one performed from a lower (smaller angle direction than incidence from a high angle side, and light reception on a low angle side means one performed in a lower (smaller) angle direction than light reception on a high angle side. That is, directions in which incidence and light reception on a low angle side, and incidence and light reception on a high angle side are performed in the present invention are determined in a relative manner, and angles are not limited. Preferably, in an embodiment, the incidence from a low angle side means causing light to enter a surface from a direction of 20°±15° while defining the entire direction horizontal to a surface of an epitaxial wafer to be evaluated as 0° and the direction vertical to the surface as 90°, and light reception on a low angle side means receiving light in a direction within the range of 0° to 80°. On the other hand, preferably, in an embodiment, incidence from a high angle side means causing light to enter a surface from a higher angle direction than incidence from a low angle side, and causing light to enter a surface from a direction of 90°±20°, and light reception on a high angle side means light reception in a higher angle direction than light reception on a low angle side, and means light reception in a direction within a range of more than 80° to 90°.

In an embodiment, incidence and light reception from a high angle side for obtaining the measurement result 2 can be performed in the direction vertical to a surface of an epitaxial wafer to be evaluated. In the present invention, the vertical direction is used in the sense of including directions in a range considered to be approximately equal to the direction of 90° (the completely vertical direction), for example, directions of 90°±5° while defining the entire direction horizontal to a surface of an epitaxial wafer to be evaluated as 0°. Among laser surface inspection apparatuses, there is an apparatus in which a light receiving system configured so as not to receive light entering from the vertical direction to a surface of an object to be evaluated and being reflected to the same direction as the incident direction, that is, light that is specularly reflected, by a light-shielding unit such as a slit, filter or the like. When such a laser surface inspection apparatus is used, light that enters from a direction of 90° to a surface of an epitaxial wafer to be evaluated (the completely vertical direction) and that is reflected to the same direction as the incident direction (specularly reflected light) is not included in the light received by the light receiving system.

(Abnormal Substance to be Detected)

Targets to be evaluated in the above evaluation method are abnormal substances selected from the group consisting of defects and surface deposits of an epitaxial wafer to be evaluated. Such abnormal substances are detected as a light point defect in the light receiving system by making light incident onto the epitaxial wafer to be evaluated and by radiating (scattering or reflecting) the light from the wafer surface, as described above. The size (detection size) of the abnormal substance on the wafer having caused the light point defect can be calculated on the basis of the size of the standard particle in the calculation part of the surface inspection apparatus, by detecting the light point defect. The calculation of the detection size based on the size of the standard particle can be performed by a calculation unit provided in a commercially available surface inspection apparatus or by a known calculation method.

Abnormal substances that may exist in an epitaxial wafer are roughly classified into an epitaxial layer-derived defect resulting from an epi-layer (epitaxial layer) and a foreign substance not resulting from the epi-layer (non-epitaxial layer-derived foreign substance). As epitaxial layer-derived defects, for example, Hillock, Stacking Fault (SF), Dislocation (observed as Shadow) and the like are known. On the other hand, non-epitaxial layer-derived foreign substances are surface deposits that are adhering substances that can be removed by washing, such as a particle adhering to a wafer surface. In an embodiment, abnormal substances detected by the above evaluation method include epitaxial layer-derived defects and non-epitaxial layer-derived foreign substances.

Since the epitaxial layer-derived defect and the non-epitaxial layer-derived foreign substance have different causes of generation, managements of manufacturing processes for reducing them are different from each other. Therefore, in the evaluation of an epitaxial wafer, the epitaxial layer-derived defect and the non-epitaxial layer-derived defect can be desirably detected while making a distinction between them. However, in the conventional defect evaluation methods of a semiconductor wafer, it has not been easy to detect an epitaxial layer-derived defect and a non-epitaxial layer-derived foreign substance while making a distinction between them. Reasons therefor include that the non-epitaxial layer-derived foreign substance is observed in a convex shape on a surface of an epitaxial wafer, and that the epitaxial layer-derived defects also include a defect observed in a convex shape. In contrast, according to an embodiment of the above evaluation method, it can become possible to distinguish an epitaxial layer-derived defect from a non-epitaxial layer-derived foreign substance by performing the evaluation based on the above kinds of measurement results (measurement result 1 and measurement result 2).

For example, in an embodiment, a non-epitaxial layer-derived foreign substance, Hillock, Stacking Fault, and Dislocation can be distinguished from each other by:

the presence or absence of detection and a detection size in the measurement result 1; and the presence or absence of detection and a detection size the measurement result 2.

In addition, in an embodiment, it is possible to determine an abnormal substance detected only in the measurement result 1 as a non-epitaxial layer-derived foreign substance, and to determine an abnormal substance detected only in the measurement result 2 as Hillock.

Furthermore, in an embodiment, among plots obtained by taking the detection size in the measurement result 1 on the X-axis and taking the detection size in the measurement result 2 on the Y-axis, a non-epitaxial layer-derived foreign substance and various epitaxial layer-derived defects can be distinguished from each other according to the standard shown in Table 1 below, on the basis of:

a correlation equation 1: $y_1 = ax_1 + b$ obtained by fitting plots in which the detection size in the measurement result 1 is within a first range; and a correlation equation 2: $y_2 = cx_2 + d$ obtained by fitting plots in which detection size in the measurement result 1 is within a second range that is a range larger than the first range among the plots. Fitting can be performed by a known fitting method such as the least-square method. As to the reason why such distinction becomes possible, the present inventor assumes that, since various abnormal substances have different shapes or sizes due to the cause of generation thereof and the like, the presence or absence of detection and a detection size in low angle incidence and low angle light reception by ultraviolet light irradiation do not necessarily become the same as the presence or absence of detection and a detection size in high angle incidence and high angle light reception by visible light irradiation. The fact that distinction of various abnormal substances becomes possible by utilizing the above-described point on the basis of the standard below obtained from the correlation equation 1 and the correlation equation 2 was newly found as a result of extensive research by the present inventor. As an example, for example, if a non-epitaxial layer-derived foreign substance (for example, a particle adhering to a wafer surface) has a complete spherical shape, the presence or absence of detection and a detection size in low angle incidence and low angle light reception by ultraviolet light irradiation is considered to coincide with the presence or absence of detection and a detection size in high angle incidence and high angle light reception by visible light irradiation. However, it is assumed that a non-epitaxial layer-derived foreign substance actually existing in an epitaxial wafer may not have a complete spherical shape. Furthermore, it is also assumed that, due to the difference in shapes, particles tend to generate isotropic scattering, whereas Stacking Fault (SF) tends to generate anisotropic scattering, and thus intensity of scattered light received by high angle light reception tends to be larger in comparison with intensity of scattered light received by low angle light reception. As a result, the present inventor assumes that, as to SF, the detection size in the measurement result 1 tends to be different from the detection size in the measurement result 2.

However, the above is assumption by the present inventor, and does not limit the present invention in any way.

TABLE 1

| Types of abnormal substance | Distinction standard |
|---|---|
| Non-epitaxial layer-derived foreign substance | detected only in the measurement result 1, or, [(detection size in measurement result 2) − d]/ (detection size in measurement result 1) ≤ c |
| Hillock | detected only in the measurement result 2 |
| Stacking Fault | [(detection size in measurement result 2) − b]/ (detection size in measurement result 1) < a, and, [(detection size in measurement result 2) − d]/ (detection size in measurement result 1) > c |

TABLE 1-continued

| Types of abnormal substance | Distinction standard |
|---|---|
| Epitaxial layer-derived defect selected from the group consisting of Hillock and Dislocation | [(detection size in measurement result 2) − b]/ (detection size in measurement result 1) ≥ a |

In an embodiment, the first range is a range of more than 0 μm and less than 0.1 μm, and the second range is a range of equal to or more than 0.1 μm and equal to or less than 0.2 μm. However, the ranges are not limited to the above ranges. By obtaining the correlation equation 1 and the correlation equation 2 from plots within the first range and plots within the second range that is a larger range than the first range, various types of abnormal substances can be distinguished according to the standard shown in the Table 1 on the basis of the measurement results 1 and 2, and the correlation equations.

A further specific embodiment of the above evaluation method will be described later on the basis of Examples.

By performing a process change or maintenance (for example, change in manufacturing conditions, exchange of manufacturing equipment, washing, quality enhancement of chemical liquid, and the like) for reducing various abnormal substances for manufacturing processes of an epitaxial wafer on the basis of the evaluation results obtained by performing the evaluation by the above evaluation method, it becomes subsequently possible to provide an epitaxial wafer having a few number of abnormal substances and high quality, as a product wafer.

Furthermore, by evaluating epitaxial wafers before shipping as products through the use of the above evaluation method, and by shipping, as product wafers, epitaxial wafers in which existing number of various abnormal substances is confirmed to be within the allowable range having previously been determined (equal to or less than the threshold value), it becomes possible to stably supply epitaxial wafers having high quality. The threshold value is not particularly limited, and can be appropriately set in accordance with the uses or the like of a product wafer.

That is, the above evaluation method can be used for a process management or quality control of epitaxial wafers.

Evaluation Apparatus Of Epitaxial Wafer

A further aspect of the present on relates to an apparatus of evaluating an epitaxial wafer, which includes two types of incidence systems with different incidence angles and two types of light receiving systems with different light receiving angles, and which is used in the above evaluation method. Details thereof are as described above.

Epitaxial Wafer

A further aspect of the present invention relates to an epitaxial wafer having been subjected to the evaluation according to the above evaluation method. The above epitaxial wafer can be an epitaxial wafer in which the existence number of various types of abnormal substances is confirmed to be within the allowable range having previously determined (equal to or less than the threshold value) by the evaluation according to the above evaluation method.

EXAMPLES

The present invention will be described in detail below based on Examples. However, the present invention is not limited to the embodiments shown in Examples.

1. Detection of Light Point Defect (LPD), Size Calculation of Abnormal Substance A Surfscan Series SP3 (light source wavelength: 266 nm) manufactured by KLA TENCOR was used as a surface inspection apparatus for obtaining the measurement result 1, in the HSO (High Sensitivity Oblique) mode and the DWO channel (Dark Field Wide Oblique Channel) of the apparatus.

A Surfscan, Series SP1 (light source wavelength: 488 manufactured by KLA TENCOR was used as a surface inspection apparatus for obtaining the measurement result 2, in the HSN (High. Sensitivity Normal) mode and the DNN channel (Dark Field Narrow Normal Channel) of the apparatus.

Through the use of the surface inspection apparatuses, incident light was scanned on the whole surface area of the epitaxial layer surface of a p/p silicon epitaxial wafer (epitaxial layer thickness: 4 μm) having a diameter of 300 mm to thereby detect light point defects (LPD), and sizes of the abnormal substances detected were calculated by a calculation part provided in the surface inspection apparatuses on the basis of sizes of detected light point defects.

2. Calculation of Correlation Equation 1 and Correlation Equation 2

Through the use of the measurement result 1 and the measurement result 2 obtained in the above 1, plots were made on a graph for the respective light point defects, while taking the detection size in the measurement result 1 on the X-axis and taking the detection size in measurement result 2 on the Y-axis.

While setting the first range as a range of more than 0 μm and less than 0.1 μm and setting the second range as a range of equal to or more than 0.1 μm and equal to or less than 0.2 μm, the correlation equation 1 was calculated by fitting, by the least-square method, plots, the detection size of which in the measurement result 1 is within the first range among the plots that have been made, and the correlation equation 2 was calculated by fitting, by the least-square method, plots the detection size of which in the measurement result 1 is within the second range being a range larger than the first range.

Figure 2:
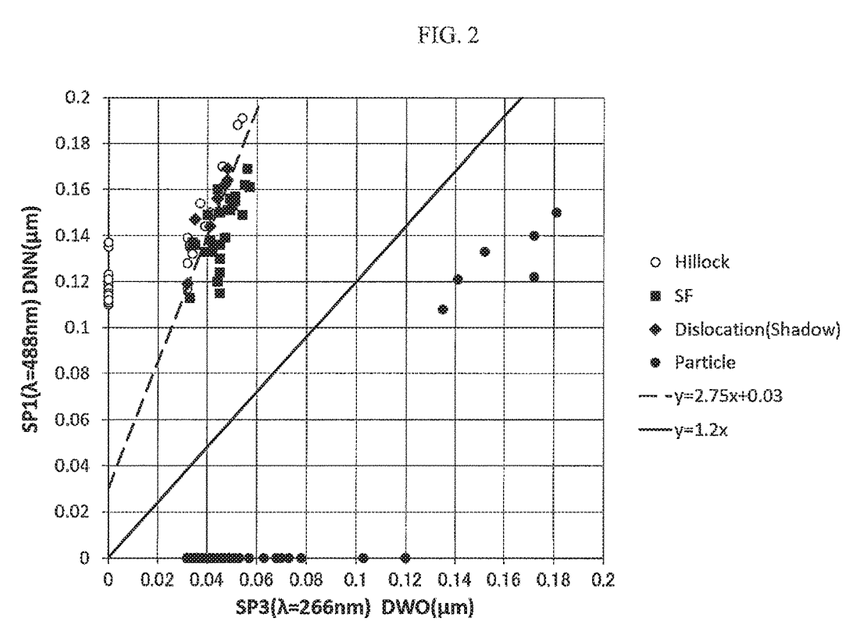
FIG. 2 is a graph showing evaluation results of an epitaxial wafer in Examples.

The calculated correlation equations were as follows. Therefore, in Table 1 shown above, a=2.75, b=0.03, c=1.20, and d=0 hold.

$$y=2.75x+0.03 \quad \text{Correlation Equation 1:}$$

$$y=1.20x \quad \text{Correlation equation 2:}$$

3. Distinction of Abnormal Substance by Actual Observation

The epitaxial layer surface of the epitaxial wafer subjected to the above evaluation was observed with a wafer defect inspection and review apparatus MAGICS (manufactured by Lasertec Corporation), a Review-SEM (Review scanning electron microscope) and an AFM (atomic force microscope), and abnormal substances existing at the position of light point defects detected by the surface inspection apparatus were identified on the basis of the observed shape.

In FIG. 2, the correlation equation 1, the correlation equation 2 and types of abnormal substances corresponding to respective plots identified in the above-described 3. are shown. From FIG. 2, it can be confirmed that the distinction of various types of abnormal substances is possible on the basis of the standard shown in above-described Table 1.

An aspect of the present invention can be useful in the field of manufacturing epitaxial wafers.

Although the present invention has been described in considerable detail with regard to certain versions thereof, other versions are possible, and alterations, permutations and equivalents of the version shown will become apparent to those skilled in the art upon a reading of the specification and study of the drawings. Also, the various features of the versions herein can be combined in various ways to provide additional versions of the present invention. Furthermore, certain terminology has been used for the purposes of descriptive clarity, and not to limit the present invention, Therefore, any appended claims should not be limited to the description of the preferred versions contained herein and should include all such alterations, permutations, and equivalents as fall within the true spirit and scope of the present invention.

Having now fully described this invention, it will be understood to those of ordinary skill in the art that the methods of the present invention can be carried out with a wide and equivalent range of conditions, formulations, and other parameters without departing from the scope of the invention or any embodiments thereof.

All patents and publications cited herein are hereby fully incorporated by reference in their entirety. The citation of any publication is for its disclosure prior to the filing date and should not be construed as an admission that such publication is prior art or that the present invention is not entitled to antedate such publication by virtue of prior invention.

What is claimed is:

1. A method of evaluating an epitaxial wafer, comprising:
performing evaluation of the epitaxial wafer by detecting, as a light point defect, an abnormal substance selected from the group consisting of a defect and a surface deposit of the epitaxial wafer to be evaluated,
wherein the evaluation of the epitaxial wafer is performed with a surface inspection apparatus including two types of incidence systems with different incidence angles and two types of light receiving systems with different light receiving angles,
wherein, among the two types of incidence systems, the incidence system with an incident angle smaller than the incident angle of the other incidence system is referred to as a low angle side incidence system and the other incidence system is referred to as a high angle side incidence system, and among the two types of light receiving systems, the light receiving system with a light receiving angle smaller than the light receiving angle of the other light receiving system is referred to as a low angle side light receiving system and the other light receiving system is referred to as a high angle side light receiving system, and
wherein the performing evaluation of the epitaxial wafer is based on
a first measurement based on low angle incidence and low angle light reception, the first measurement being obtained by causing ultraviolet light to enter a surface of the epitaxial wafer to be evaluated from the low angle side incidence system and receiving radiation light from the surface on the low angle side light receiving system; and
a second measurement based on high angle incidence and high angle light reception, the second measurement being obtained by causing visible light to enter the surface of the epitaxial wafer to be evaluated from the high angle side incidence system and receiving radiation light from the surface on the high angle side light receiving system.

2. The method of evaluating the epitaxial wafer according to claim 1, wherein the high angle incidence and high angle light reception is performed in a direction vertical to the surface of the epitaxial wafer to be evaluated.

3. The method of evaluating the epitaxial wafer according to claim 2, wherein the abnormal substance is selected from the group consisting of an epitaxial layer-derived defect and a non-epitaxial layer-derived foreign substance.

4. The method of evaluating the epitaxial wafer according to claim 2, which further comprises distinguishing a non-epitaxial layer-derived foreign substance, Hillock, Stacking Fault, and Dislocation by:

presence or absence of detection and a detection size in the first measurement; and presence or absence of detection and a detection size in the second measurement.

5. The method of evaluating the epitaxial wafer according to claim 4, wherein the distinguishing comprises determining an abnormal substance detected only in the first measurement as the non-epitaxial layer-derived foreign substance and/or determining an abnormal substance detected only in the second measurement as Hillock.

6. The method of evaluating the epitaxial wafer according to claim 4, wherein the distinguishing is performed according to the standard shown in Table 1 below:

TABLE 1

| Types of abnormal substance | Distinction standard |
|---|---|
| Non-epitaxial layer-derived foreign substance | detected only in the first measurement, or, [(detection size in the second measurement) − d]/ (detection size in the first measurement) ≤ c |
| Hillock | detected only in the second measurement |
| Stacking Fault | [(detection size in the second measurement) − b]/ (detection size in the first measurement) < a, and, [(detection size in the second measurement) − d]/ (detection size in the first measurement) > c |
| Epitaxial layer-derived defect selected from the group consisting of Hillock and Dislocation | [(detection size in the second measurement) − b]/ detection size in the first measurement) ≥ a | based on a correlation equation 1: $y_1=ax_1+b$ obtained by fitting plots, the detection size of which in the first measurement is within a first range, and a correlation equation 2: $y_2=cx_2+d$ obtained by fitting plots the detection size of which in the first measurement is within a second range that is a range larger than the first range among plots, the plots being obtained by taking the detection size in the first measurement on an X-axis and taking the detection size in the second measurement on a Y-axis.

7. The method of evaluating the epitaxial wafer according to claim 6, wherein the first range is a range of more than 0 µm and less than 0.1 µm, and the second range is a range of equal to or more than 0.1 µm and equal to or less than 0.2 µm.

8. The method of evaluating the epitaxial wafer according to claim 1, wherein the abnormal substance is selected from the group consisting of an epitaxial layer-derived defect and a non-epitaxial layer-derived foreign substance.

9. The method of evaluating the epitaxial wafer according to claim 8, which further comprises distinguishing the non-epitaxial layer-derived foreign substance, Hillock, Stacking Fault, and Dislocation by:

presence or absence of detection and a detection size in the first measurement; and presence or absence of detection and a detection size in the second measurement.

10. The method of evaluating the epitaxial wafer according to claim 9, wherein the distinguishing comprises determining an abnormal substance detected only in the first measurement as the non-epitaxial layer-derived foreign substance and/or determining an abnormal substance detected only in the second measurement as Hillock.

11. The method of evaluating the epitaxial wafer according to claim 9, wherein the distinguishing is performed according to the standard shown in Table 1 below:

TABLE 1

| Types of abnormal substance | Distinction standard |
|---|---|
| Non-epitaxial layer-derived foreign substance | detected only in the first measurement, or, [(detection size in the second measurement) − d]/ (detection size in the first measurement) ≤ c |
| Hillock | detected only in the second measurement |
| Stacking Fault | [(detection size in the second measurement) − b]/ (detection size in the first measurement) < a, and, [(detection size in the second measurement) − d]/ (detection size in the first measurement) > c |
| Epitaxial layer-derived defect selected from the group consisting of Hillock and Dislocation | [(detection size in the second measurement) − b]/ (detection size in the first measurement) ≥ a | based on a correlation equation 1: $y_1=ax_1+b$ obtained by fitting plots, the detection size of which in the first measurement is within a first range, and a correlation equation 2: $y_2=cx_2+d$ obtained by fitting plots, the detection size of which in the first measurement is within a second range that is a range larger than the first range among plots, the plots being obtained by taking the detection size in the first measurement on an X-axis and taking the detection size in the second measurement on a Y-axis.

12. The method of evaluating the epitaxial wafer according to claim 11, wherein the first range is a range of more than 0 µm and less than 0.1 µm, and the second range is a range of equal to or more than 0.1 µm and equal to or less than 0.2 µm.

13. The method of evaluating the epitaxial wafer according to claim 1, which further comprises distinguishing a non-epitaxial layer-derived foreign substance, Hillock, Stacking Fault, and Dislocation by:

presence or absence of detection and a detection size in the first measurement; and presence or absence of detection and a detection size in the second measurement.

14. The method of evaluating the epitaxial wafer according to claim 13, wherein the distinguishing comprises determining an abnormal substance detected only in the first measurement as a non-epitaxial layer-derived foreign substance and/or determining an abnormal substance detected only in the second measurement as Hillock.

15. The method of evaluating the epitaxial wafer according to claim 13, wherein the distinguishing is performed according to the standard shown in Table 1 below:

TABLE 1

| Types of abnormal substance | Distinction standard |
|---|---|
| Non-epitaxial layer-derived foreign substance | detected only in the first measurement, or, [(detection size in the second measurement − d]/(detection size in the first measurement) ≤ c |
| Hillock | detected only in the second measurement |
| Stacking Fault | [(detection size in the second measurement) − b]/(detection size in the first measurement) < a, and, [(detection size in the second measurement) − d]/(detection size in the first measurement) > c |
| Epitaxial layer-derived defect selected from the group consisting of Hillock and Dislocation | [(detection size in the second measurement) − b]/(detection size in the first measurement) ≥ a | based on a correlation equation 1: $y_1=ax_1+b$ obtained by fitting plots, the detection size of which in the first measurement is within a first range, and a correlation equation 2: $y_2=cx_2+d$ obtained by fitting plots, the detection size of which in the first measurement is within a second range that is a range larger than the first range among plots, the plots being obtained by taking the detection size in the first measurement on an X-axis and taking the detection size in the second measurement on a Y-axis.

16. The method of evaluating the epitaxial wafer according to claim 15, wherein the first range is a range of more than 0 μm and less than 0.1 μm, and the second range is a range of equal to or more than 0.1 μm and equal to or less than 0.2 μm.

* * * * *